United States Patent
Hee et al.

(10) Patent No.: US 9,829,476 B2
(45) Date of Patent: Nov. 28, 2017

(54) MEASUREMENT METHOD AND DEVICE, FOR DETERMINING DEGREE OF ENGINE OIL DILUTION BY FAME

(71) Applicant: YANMAR CO., LTD., Osaka-shi, Osaka (JP)

(72) Inventors: Kay Kian Hee, Sabah (MY); Kamaruddin Kudumpor, Sabah (MY); Beverly Kah Waynee, Sabah (MY); Siti Norbaria Sally Bt. Pick Thall Tan, Sabah (MY); Aaron Willinton William, Sabah (MY)

(73) Assignee: YANMAR, Kota Kinabalu, Sabah (MY)

( * ) Notice: Subject to any disclaimer, the term of this patent is extended or adjusted under 35 U.S.C. 154(b) by 37 days.

(21) Appl. No.: 14/386,045

(22) PCT Filed: Jan. 22, 2013

(86) PCT No.: PCT/JP2013/051221
§ 371 (c)(1),
(2) Date: Sep. 18, 2014

(87) PCT Pub. No.: WO2013/140843
PCT Pub. Date: Sep. 26, 2013

(65) Prior Publication Data
US 2015/0044775 A1    Feb. 12, 2015

(30) Foreign Application Priority Data
Mar. 19, 2012    (MY) .............................. PI2012001237

(51) Int. Cl.
*G01N 33/30*    (2006.01)
*G01N 33/28*    (2006.01)

(52) U.S. Cl.
CPC ......... *G01N 33/30* (2013.01); *G01N 33/2888* (2013.01)

(58) Field of Classification Search
CPC ..................................................... G01N 33/30
See application file for complete search history.

(56) References Cited

U.S. PATENT DOCUMENTS 3,810,737 A * 5/1974 Geist et al. .......... G01N 33/146
                                                              422/510
4,388,407 A    6/1983 Lepain et al.
(Continued)

FOREIGN PATENT DOCUMENTS

DE    2212185 A1    9/1973
JP    58062559 A    4/1983
(Continued)

OTHER PUBLICATIONS

Extended European Search Report for corresponding European Application No. EP13763718.7-1559 /2829874 PCT/JP2013051221; dated Oct. 13, 2015.
(Continued)

*Primary Examiner* — Lyle Alexander
*Assistant Examiner* — Dwan A Gerido
(74) *Attorney, Agent, or Firm* — Cantor Colburn LLP

(57) ABSTRACT

For checking engine oil, especially containing rate of FAME (Fatty Acid Methyl Ester), we provide a measuring device including a cylindrical and upright analysis vessel having a reading scale with which a surface boundary is measured. In the vessel, the engine oil is mixed with reagents including alcohol(s) and a demulsifier. And the decreased volume is checked as volume of the FAME contained in the engine oil.

2 Claims, 6 Drawing Sheets

(56) References Cited

U.S. PATENT DOCUMENTS

| | | | |
|---|---|---|---|
| 6,017,369 A | 1/2000 | Ahmed | |
| 6,190,427 B1 | 2/2001 | Ahmed | |
| 6,306,184 B2 | 10/2001 | Ahmed | |
| 7,927,877 B1* | 4/2011 | Kauffman | G01N 33/2835 436/164 |
| 2001/0003881 A1 | 6/2001 | Ahmed | |
| 2002/0092228 A1 | 7/2002 | Ahmed | |
| 2006/0192122 A1 | 8/2006 | Chen et al. | |
| 2010/0015716 A1 | 1/2010 | Lecointe | |

FOREIGN PATENT DOCUMENTS

| | | |
|---|---|---|
| JP | I31587 B2 | 6/1989 |
| JP | 2002530515 A | 9/2002 |
| JP | 2003156445 A | 5/2003 |
| JP | 2005337096 A | 12/2005 |
| JP | 2008220319 A | 9/2008 |
| JP | 2009541729 | 11/2009 |
| JP | 2012052903 A | 3/2012 |

OTHER PUBLICATIONS

Dobashi, Keiichi, "Impact of Bio Diesel Fuels on Diesel Engine Oil Performance"; Journal of Japanese Society of Tribologists, pp. 217-322, vol. 55, 2010; with partial English translation.
International Search Report for International Application No. PCT/JP2013/051221; dated, Mar. 5, 2013; with English translation.
European Patent Office Examination Report corresponding to European Patent Application No. 13763718.7-1559; dated: Dec. 12, 2016.

\* cited by examiner

FIG. 1 - Basic Idea of measurement of Engine Oil Dilution by FAME for FD5 & FD10

FIG. 2 - Side View of Measuring Vessel

Fuel Dilution Test Kit Set

MEASUREMENT METHOD AND DEVICE, FOR DETERMINING DEGREE OF ENGINE OIL DILUTION BY FAME

This is the U.S. national stage of application No. PCT/JP2013/051221, filed on Jan. 22, 2013. Priority under 35 U.S.C. §119(a) and 35 U.S.C. §365(b) is claimed from Malaysian Application No. PI2012001237, filed Mar. 19, 2012, the disclosure of which is also incorporated herein by reference.

TECHNICAL FIELD

The present invention relates to measuring method and a measuring device for measuring the FAME content in engine oil. Biodiesel has a higher and narrower boiling range than regular diesel fuel, and because of its molecular structure, droplet sizes coming out of the fuel injectors are larger. The physical properties of biodiesel facilitate fuel dilution in the crankcase and increase the potential for engine wear. So, while the mineral diesel portion of the fuel blend vaporizes and follows its destination to the exhaust stream, the piston is at the bottom of the cylinder and the methyl ester fraction with its higher, narrower boiling range and larger droplet size remains in liquid form, collecting along the exposed surface area of the cylinder wall. As the piston rises, much of the biodiesel can bypass the oil rings and enter the crankcase. Once there, biodiesel doesn't volatilize as does mineral diesel. Combined with heat inside the crankcase, there is concern about oxidation of the oil/biodiesel mix and subsequent engine wear from organic acids.

BACKGROUND OF INVENTION

It is an object of the present invention to provide a fast measuring method and a measuring device for measuring the FAME content in engine oil. For conventional measuring methods and measuring devices for fuel dilution are specified by ASTM in the United States. Fuel dilution was measured by gas chromatography (GC) following ASTM method D3524 to measure diesel content in engine oil which provides a means to determine the magnitude of the fuel dilution, providing the user with the ability to predict performance and to take appropriate action. Fourier transform infrared (FTIR) spectrometry following a modified ASTM method D7371 to measure biodiesel content has also been utilized currently.

However, the problem and limitation of current analysis technology are cost and the availability of advanced facilities which is not available on engine operation site. The present invention has been made to facilitate the on-site measurement of the FAME content in engine oil and portable device for on-site fast check Patent Citation 1: US2006/0192122, Apparatus and Method For Measuring Fuel Dilution of Lubricant, shows an apparatus and methods for spectroscopic analysis of a petroleum product, including detecting and quantifying fuel dilution in oil sample.

DISCLOSURE OF INVENTION

Technical Problem

Conventional measuring methods and measuring devices for measuring the FAME content in engine oil cause the following problems. The analysis methods and analysis devices utilizing chromatography and FTIR require expertise and specialized skills. This makes it difficult to carry out on-site analysis. The analysis devices utilizing gas chromatography and FTIR are costly and the analysis cost involved is also high. The present invention can solve all above problem with providing fast, simple and affordable on-site fast check analysis in measuring FAME content in engine oil.

Technical Solution

According to the embodiment of the present invention, a measuring method and a measuring device for measuring FAME content in engine oil as a basic concept, and the difference in dissolving properties of FAME & Engine oil in various organic solvent.

FIG. 1 shows a method of the invention. For measuring FAME included in engine oil, alcohol is added in to the engine oil, mixed and stayed. This makes FAME separate from engine oil and introduce to the alcohol. Some additive may be included in the alcohol for accelerating the division of FAME from engine oil. And measuring surface boundary of engine oil before and after mixing shows the volume of FAME. Thus the decreased volume of engine oil after mixing with the alcohol is estimated as the volume of FAME.

As shown in FIG. 1, a special analysis vessel is used as analysis kit in the measuring method and for the measuring device for measuring FAME content in engine oil. Reagents that are used are a reagent (A) (for FAME content), a reagent (B) (as additive) and a reagent (C) (as cleaning detergent).

It is needed to find solvents not dissolving engine oil but dissolving FAME. Table 1 shows nature or alcohols.

TABLE 1

| | FAME (Carodiesel) | | | Engine Oil (Yanmar Super Royal 10W-30) | | |
|---|---|---|---|---|---|---|
| | Ratio - Alcohols:FAME, Engine Oil | | | | | |
| Alcohol | 1:1 | 5:1 | 10:1 | 1:1 | 5:1 | 10:1 |
| Methanol | ○ | ○ | ○ | ● | ● | ● |
| Ethanol | ○ | ○ | ○ | ● | ● | ● |
| Propanol | ○ | ○ | ○ | ▲ | ▲ | ▲ |
| Isopropanol | ○ | ○ | ○ | ◆ | ◆ | ◆ |
| Butanol | ○ | ○ | ○ | ○ | ○ | ○ |
| Decanol | ○ | ○ | ○ | ○ | ○ | ○ |
| Acetone | ○ | ○ | ○ | ○ | ○ | ○ |
| Toluene | ○ | ○ | ○ | ○ | ○ | ○ |

○: complete dissolve
▲: 0~20% dissolve
◆: 20~80% dissolve
●: Not dissolve

Inventors have tried several solvents that dissolve FAME but engine oil. And they found useful solvents for measuring FAME included in engine oil. Alcohol and engine oil mixtures (ratio Alcohol:engine oil; 1:1, 5:1, 10:1) and Alcohol and FAME mixtures (ratio Alcohol:FAME; 1:1, 5:1, 10:1) are tested. Table 1 shows abilities of alcohols. Methanol, ethanol and propanol are good for measuring FAME in engine oil.

[Chemical Solvent Recipe]

Following reagents are used for examination for checking ability to dissolve FAME but engine oil.

Reagent A: Methanol, ethanol & any mixture composition of methanol and ethanol

Reagent B: Parafinic oil-based demulsifier

Reagent C: Toluene, Isopropanol & any mixture composition of Toluene and Isopropanol Optimum Ratio: A-3 mL: B-1 mL: Sample-1 mL According to one aspect of the present invention, a measuring device is for measuring FAME content in engine oil. The measuring device includes a cylindrical and upright analysis vessel and a lid. The analysis vessel includes a transparent vessel. The analysis vessel includes a larger diameter portion (upper portion for reagent) and a smaller diameter portion (lower for reading scale which surface boundary is measured). The lid is on a top end of the larger portion. The surface boundary is measured with the reading scale such that measuring device receives the used engine oil sample, reagent (A) and reagent (B) through reagent inlet portion, and is shaken with the lid on and is left stand for a predetermined period of time. In the foregoing aspect of the present invention, the reagent (A) may include methanol and ethanol as main components. Reagent (B) as additives may include as demulsifier components. In the foregoing aspect of the present invention, the analysis vessel may be configured to measure FAME content in engine oil. As an additional advantageous effect, the analysis vessel is recyclable after reagent (C) is used for cleaning analysis vessel to enable it for next sample.

Thus, a measuring device of this invention has an analysis vessel with scale, a lid, and at least 2 reagents. One of reagents includes at least one of the alcohols selected from the group consisting of methanol, ethanol and propanol mixtures thereof and the other reagent includes at least a demulsifier component. And a measuring method of this invention has a step introducing engine oil, a first reagent and second reagent to an analysis vessel, a step shaking the analysis vessel, a step keeping the analysis vessel stand for a predetermined period of time, and a step measuring a surface boundary with a reading scale.

EXPLANATION OF REFERENCE 1 measuring vessel
11 top part
12 larger diameter portion
13 reading scale
14 bottom portion

BEST MODE FOR CARRYING OUT THE INVENTION

Measurement of the FAME percentage in engine oil is described as follow.

Reagent A is Methanol, ethanol or any mixture composition of methanol and ethanol. Reagent B is Parafinic oil-based demulsifier. Reagent C is Toluene, Isopropanol or any mixture composition of Toluene and Isopropanol.

Figure 3:
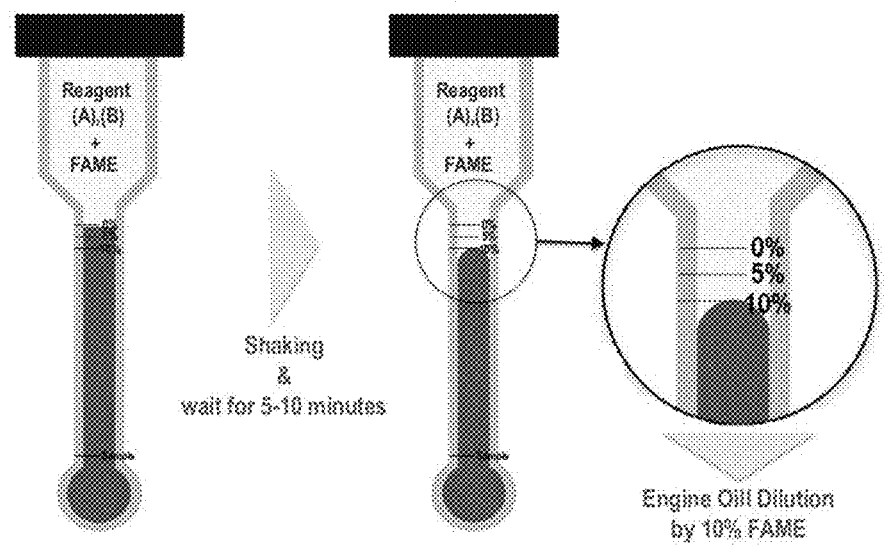
FIG. 3 is a diagram illustrating states before and after the measuring method for measuring the FAME % in engine oil according to the embodiment of the present invention.

First, used engine oil sample are added into the measuring vessel until sample line, indicating a specified amount. Next, reagent (B) is poured into the measuring vessel followed by reagent (A). The measuring vessel is shaken moderately with lid on and is stayed for 5 to 10 minutes. As shown in FIG. 3, the FAME percentage is read from the surface boundary on the FAME scale. Thus the FAME % in engine oil is obtained. After that, vessel is washed with reagent (C) to clean up chemical and engine oil sample.

Optimum Ratio for the measuring was reagent A-3 mL:reagent B-1 mL:Sample-1 mL.

Figure 1:
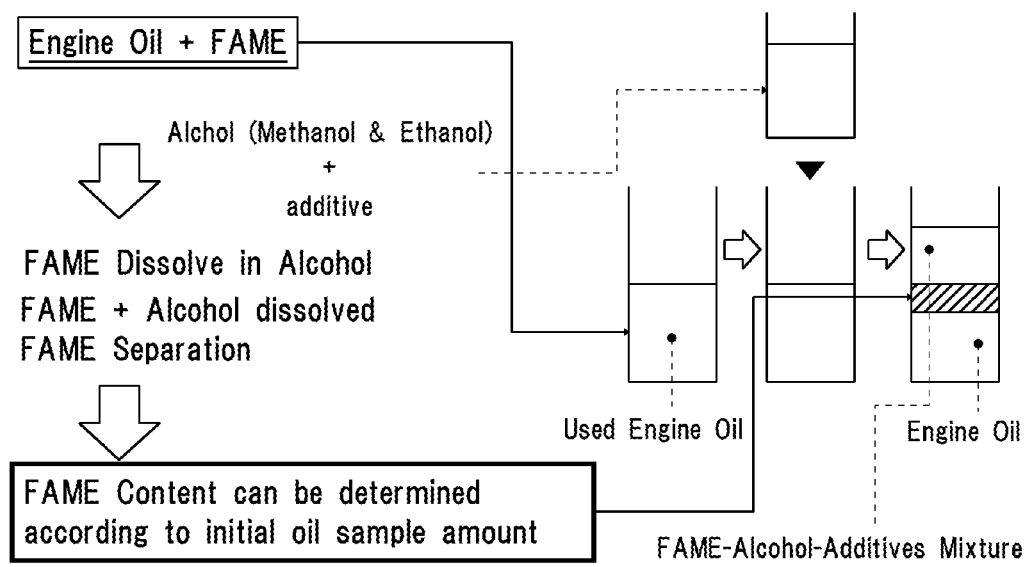
FIG. 1 is a diagram illustrating a basic concept of the measuring method for measuring the FAME % in engine oil according to the embodiment of the present invention.
Figure 2:
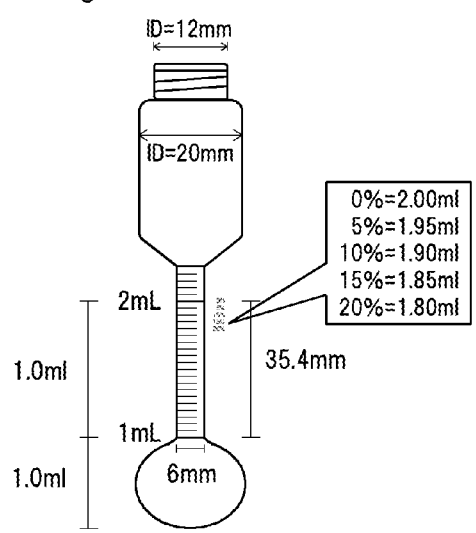
FIG. 2 is a side view of an analysis vessel used in the measuring method and measuring device for measuring FAME % in engine oil according to the embodiment of the present invention.
Figure 5:
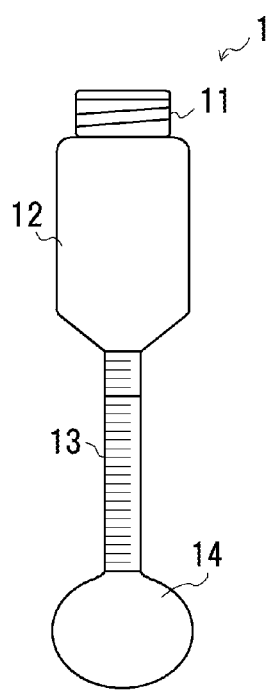
FIG. 5 is a side view of an analysis vessel for the measuring method.
Figure 6:
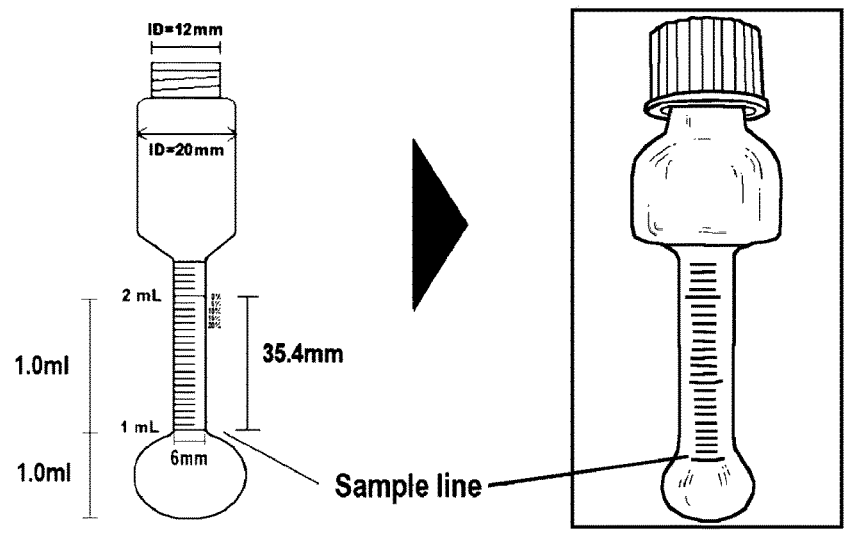
FIG. 6 is a side view of other type of analysis vessel for the measuring method.

Measuring vessel 1 is cylindrical and upright vessel. Measuring vessel 1, as shown in FIGS. 2, and 5 has a top part 11 to be put a lid, a larger diameter portion 12, a reading scale 13 is made at a lower portion and a bottom portion 14. The bottom portion 14 is made like a sphere and is made the volume large so as to be short the height of the bottom portion. The lower portion has smaller diameter than the larger diameter portion 12.

2 ml of sample, engine oil containing FAME, introduced in the measuring vessel 1 and determined volume of alcohol is added to the sample. And the measuring vessel 1 is put a lid on the top and is shaken. The reading scale 13 is made in volume range 1 ml to 2 ml or more. After shaking of the measuring vessel 1, the surface boundary between the sample and the alcohol became lower than 2 ml. The decreased volume of the sample indicates the volume of FAME contained in the sample.

FIG. 3 shows an example of measuring a sample including FAME. Sample is put into the measuring vessel up to the 0% line and Reagents A and B are added. The measuring vessel is shaken and left 5 to 10 minutes. Then the surface boundary drop and the reading scale is checked nearest the surface boundary. The surface boundary indicates 10% in FIG. 3. Thus the sample is measured as engine oil including 10% FAME.

Figure 4:
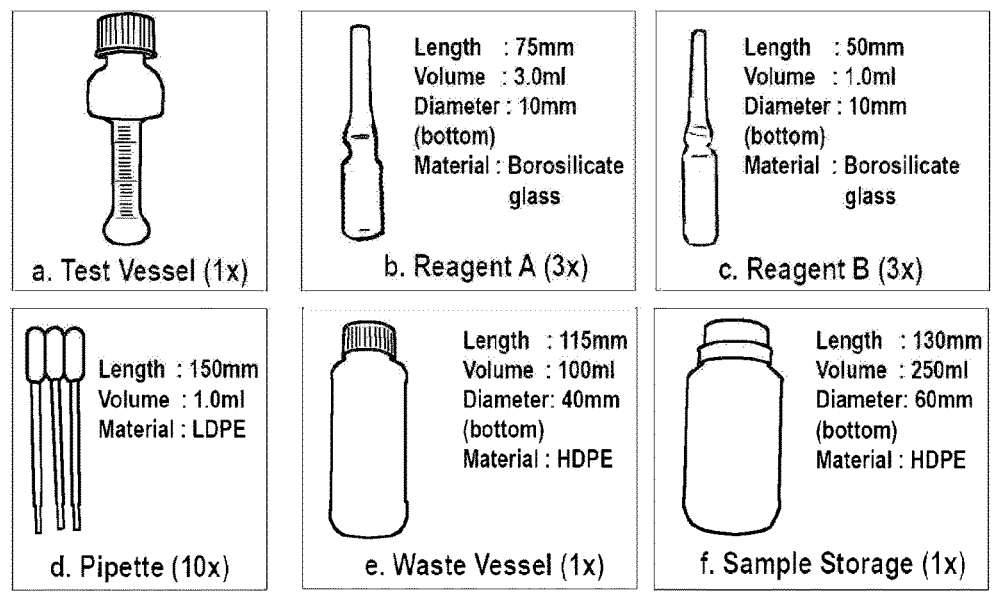
FIG. 4 shows a fuel dilution test kit set for the measuring method.

FIG. 4 shows a fuel dilution test kit set. The kit set includes one test vessel (measuring vessel), 3 of reagents A (alcohol) and B (demulsifier), 10 pipettes, one waste vessel and one sample storage.

What we claim are:

1. A measuring method for FAME (Fatty Acid Methyl Ester) in engine oil including
a step of introducing a specified amount of engine oil up to a sample line, a first reagent, and a second reagent to an analysis vessel,
a step of shaking the analysis vessel,
a step of keeping the analysis vessel stand for a predetermined period of time,
a step of measuring a surface boundary with a reading scale,
a step of measuring decreased volume of engine oil, and
a step of estimating volume of FAME,
wherein the first reagent includes at least one alcohol selected from the group consisting of methanol, ethanol, propanol, and mixtures thereof, and
the second reagent includes at least a demulsifier component.

2. The measuring method according to claim 1, wherein the analysis vessel is a cylindrical and upright analysis vessel,
includes a transparent vessel and has a larger diameter portion which is made at upper portion for introducing the first and the second reagents, and a smaller diameter portion at lower portion for reading scale with which a surface boundary is measured.

* * * * *